US010786636B2

(12) United States Patent
Zhao et al.

(10) Patent No.: US 10,786,636 B2
(45) Date of Patent: Sep. 29, 2020

(54) ATOMIZING DEVICE AND ELECTRONIC CIGARETTE HAVING SAME

(71) Applicant: SHENZHEN FIRST UNION TECHNOLOGY CO., LTD., Shenzhen (CN)

(72) Inventors: Xiaoqiang Zhao, Shenzhen (CN); Renjin Wu, Shenzhen (CN); Yonghai Li, Shenzhen (CN); Zhongli Xu, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 236 days.

(21) Appl. No.: 15/700,218

(22) Filed: Sep. 11, 2017

(65) Prior Publication Data
US 2018/0071465 A1 Mar. 15, 2018

(30) Foreign Application Priority Data

Sep. 12, 2016 (CN) .................... 2016 2 1053783 U

(51) Int. Cl.
A24F 47/00 (2020.01)
A61M 11/04 (2006.01)
A24F 40/40 (2020.01)
A61M 15/06 (2006.01)
B05B 11/00 (2006.01)
B65B 3/04 (2006.01)
B65D 1/32 (2006.01)

(52) U.S. Cl.
CPC ........... A61M 11/042 (2014.02); A24F 40/40 (2020.01); A24F 47/008 (2013.01); A61M 15/06 (2013.01);
(Continued)

(58) Field of Classification Search
CPC .............................. A61M 11/42; A24F 47/008
(Continued)

(56) References Cited

U.S. PATENT DOCUMENTS

2015/0007836 A1* 1/2015 Li .................... A24F 47/008
131/329
2016/0007654 A1* 1/2016 Zhu .................. A24F 47/008
131/328
(Continued)

FOREIGN PATENT DOCUMENTS

CN 204670386 U 9/2015
CN 105212278 A 1/2016
(Continued)

OTHER PUBLICATIONS

European Search Report.

Primary Examiner — Eric Yaary
(74) Attorney, Agent, or Firm — IPro, PLLC

(57) ABSTRACT

The disclosure discloses an atomizing device for an electronic cigarette and an electronic cigarette having the same. The atomizing device includes: an atomizing sleeve defining an e-liquid hole; an atomizing core removably arranged in the atomizing sleeve; and a sealing mechanism including a return spring and a liquid stopper, the liquid stopper connected to the atomizing sleeve via the return spring and configured to seal the e-liquid hole. When the atomizing core is received in the atomizing sleeve, the liquid stopper overcomes an elastic force of the return spring to open the e-liquid hole; and when the atomizing core is removed from the atomizing sleeve, the liquid stopper seals the e-liquid hole under the elastic force of the return spring.

16 Claims, 2 Drawing Sheets

(52) U.S. Cl.
CPC .... *A61M 2209/045* (2013.01); *B05B 11/0097* (2013.01); *B65B 3/04* (2013.01); *B65D 1/32* (2013.01)

(58) Field of Classification Search
USPC .......................................................... 131/273
See application file for complete search history.

(56) References Cited

U.S. PATENT DOCUMENTS

| | | | |
|---|---|---|---|
| 2016/0100633 A1* | 4/2016 | Gao ..................... | A24F 47/008 131/329 |
| 2016/0183597 A1 | 6/2016 | Li et al. | |
| 2017/0006915 A1 | 1/2017 | Li et al. | |
| 2017/0071258 A1 | 3/2017 | Li et al. | |
| 2017/0311384 A1 | 10/2017 | Wu | |

FOREIGN PATENT DOCUMENTS

| | | | | |
|---|---|---|---|---|
| CN | 205196994 U | 5/2016 | | |
| CN | 205196997 U | 5/2016 | | |
| CN | 105725280 A | 7/2016 | | |
| EP | 3025602 A2 | 6/2016 | | |
| EP | 3124430 A1 | 2/2017 | | |
| EP | 3135140 A1 | 3/2017 | | |
| EP | 3235391 A1 | 10/2017 | | |
| WO | WO-2016128562 A1 * | 8/2016 | ........... | A24F 47/002 |

* cited by examiner ized sleeve, the liquid stopper 132 is pushed to overcome an elastic force of the return spring 131 to open the e-liquid

ATOMIZING DEVICE AND ELECTRONIC CIGARETTE HAVING SAME

CROSS-REFERENCE TO RELATED APPLICATIONS

The present disclosure claims priority to Chinese Patent Application No. 201621053783.0, filed with the Chinese Patent Office on Sep. 12, 2016, titled "ATOMIZING DEVICE AND ELECTRONIC CIGARETTE HAVING SAME," the entire contents of which are incorporated herein by reference.

TECHNICAL FIELD

The disclosure relates to the technical field of electronic cigarettes, and in particular, relates to an atomizing device and an electronic cigarette having the same.

BACKGROUND

As a kind of hobby and special merchandise, cigarettes are popular among people. However, tar, carbon monoxide and the like substances contained in the cigarette are hazardous to the health of people. Especially, the tar contains over ten cancer-inducing ingredients, which greatly influence the human health. At present, governments all over the world have gradually prohibited smoking cigarettes (tobaccos) in the public places. However, it is very painful and hard for addicted smokers to quit cigarettes. Therefore, many cigarette substitutes are emerging in the market, for example, cigarette cessation tablets, electronic cigarettes and the like.

The electronic cigarettes generate aerosol by atomizing cartridges, such that users smoke and feel as they are smoking real cigarettes because the electronic cigarettes have a similar appearance as the real cigarettes and create similar taste as the real cigarettes. In addition, since the electronic cigarettes contains no tar, suspension particles and the like hazardous substances, the electronic cigarettes are more and more widely welcomed by the users.

The atomizing core in the atomizing device for a conventional electronic cigarette is a replaceable unit. During replacement of the atomizing core, if e-liquid in the atomizing device is not used up and the user immediately takes out the atomizing core before performing an "inversion" operation, the e-liquid would directly leaks, thereby causing inconvenience to the user and affecting normal use.

SUMMARY

An embodiment of the disclosure provides an atomizing device for an electronic cigarette. The atomizing device includes: an atomizing sleeve, defining an e-liquid hole; an atomizing core, removably arranged in the atomizing sleeve; and a sealing mechanism, including a return spring and a liquid stopper, the liquid stopper connected to the atomizing sleeve via the return spring and configured to seal the e-liquid hole; wherein when the atomizing core is received in the atomizing sleeve, the liquid stopper overcomes an elastic force of the return spring to open the e-liquid hole; and when the atomizing core is removed from the atomizing sleeve, the liquid stopper seals the e-liquid hole under the elastic force of the return spring.

Another embodiment of the disclosure provides an electronic cigarette. The electronic cigarette includes a battery device and an atomizing device. The atomizing device includes:

an atomizing sleeve, defining an e-liquid hole;
an atomizing core, removably arranged in the atomizing sleeve, the battery device electrically connected to the atomizing core; and
a sealing mechanism, including a return spring and a liquid stopper, the liquid stopper connected to the atomizing sleeve via the return spring and configured to seal the e-liquid hole;
wherein when the atomizing core is received in the atomizing sleeve, the liquid stopper overcomes an elastic force of the return spring to open the e-liquid hole; and when the atomizing core is removed from the atomizing sleeve, the liquid stopper seals the e-liquid hole under the elastic force of the return spring.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

DETAILED DESCRIPTION

Details are given in the following description for better understanding of this disclosure. However, this disclosure may be implemented in a plurality of embodiments different from those described herein, and a person skilled in the art may make similar derivations without departing from the essence of this disclosure. Therefore, this disclosure is subject to limitations by the specific embodiments of this disclosure disclosed hereinafter.

With respect to the defects mentioned in the background, this disclosure provides an atomizing device for an electronic cigarette and an electronic cigarette having the same. This disclosure is described in detail hereinafter with reference to accompanying drawings and exemplary embodiments.

Figure 1:
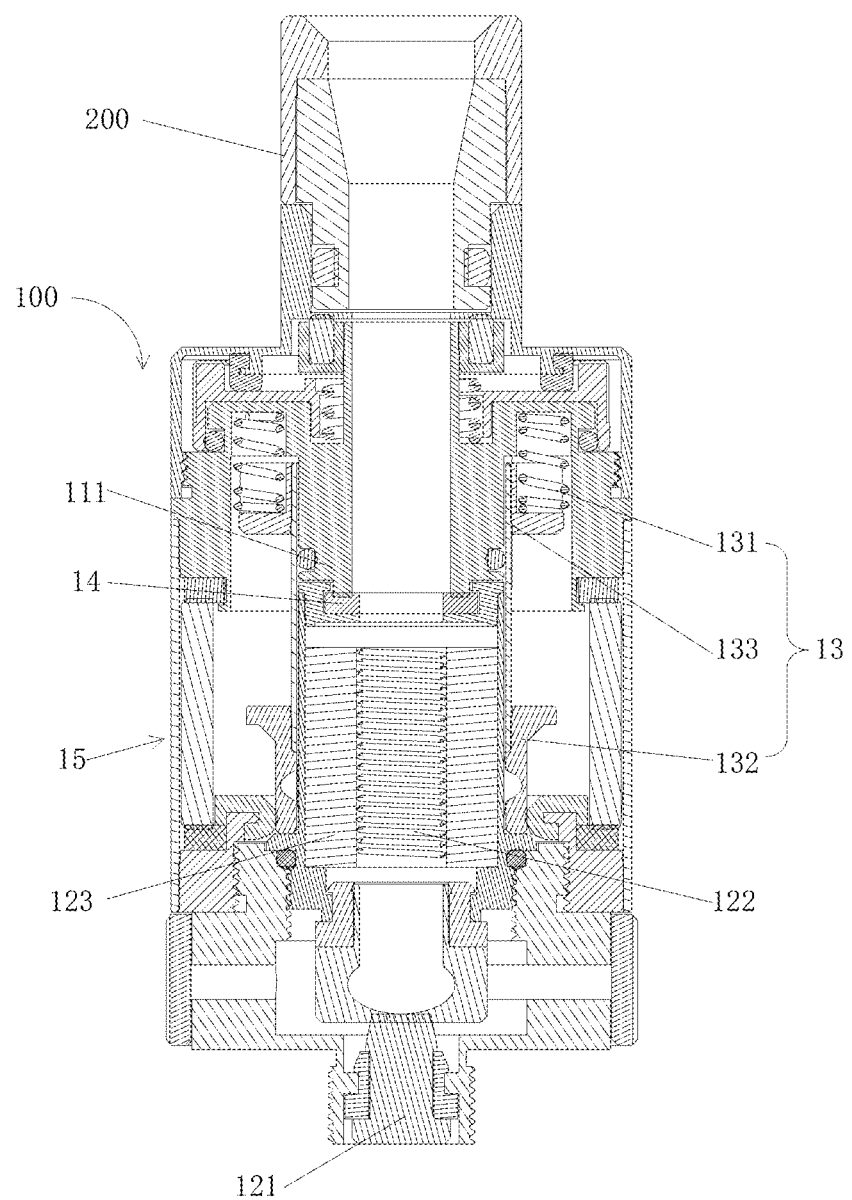
FIG. 1 is a schematic structural view of an atomizing device for an electronic cigarette in one state according to an embodiment of the disclosure.
Figure 2:
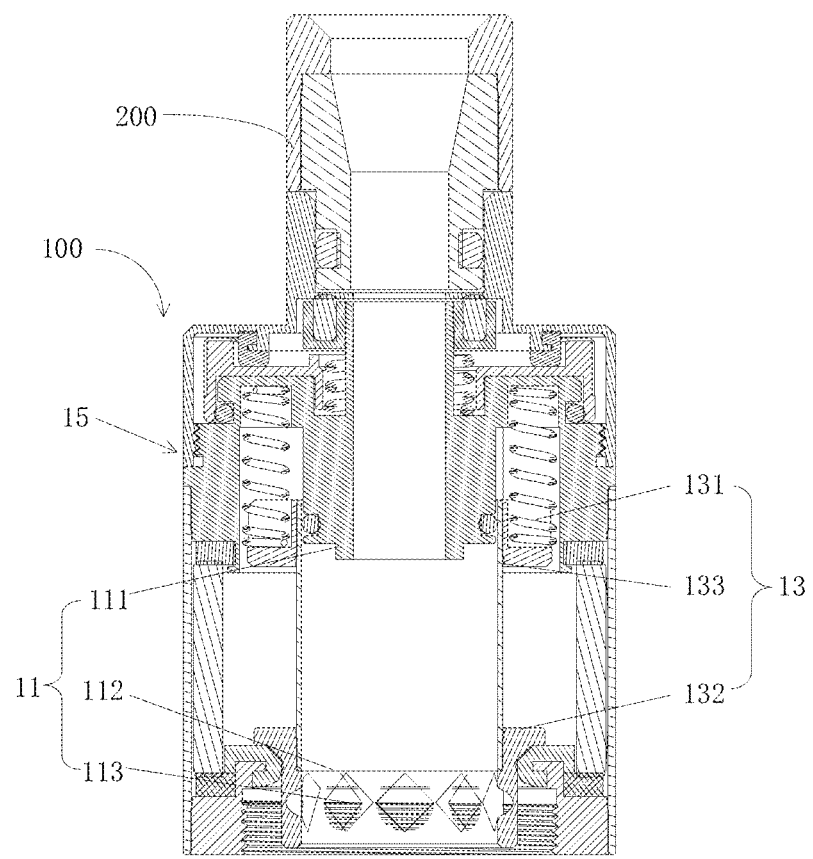
FIG. 2 is a schematic structural view of the atomizing device for an electronic cigarette in FIG. 1 in another state.
Figure 2:
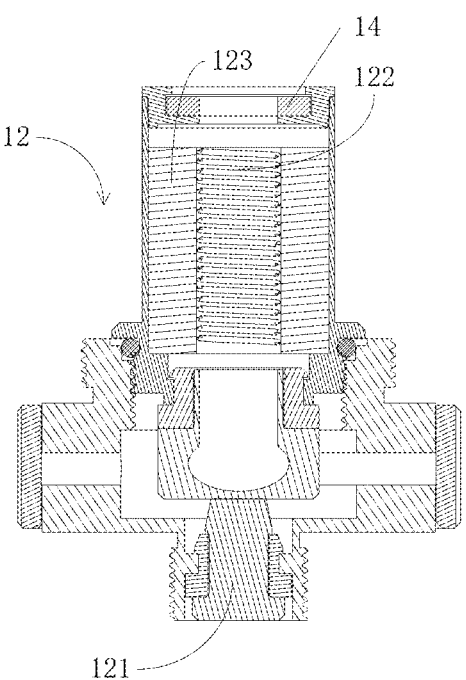

Referring to FIG. 1 and FIG. 2, FIG. 1 is a schematic structural view of an atomizing device 100 for an electronic cigarette in one state according to an embodiment of this disclosure; and FIG. 2 is a schematic structural view of the atomizing device 100 for an electronic cigarette in FIG. 1 in another state according to the embodiment of this disclosure.

In this illustrated embodiment, the atomizing device 100 includes an atomizing sleeve 11, an atomizing core 12 and a sealing mechanism 13. The atomizing sleeve 11 includes an e-liquid hole 113. If no sealing mechanism 13 is provided, during removing of the atomizing core 12 from the atomizing sleeve 11, e-liquid may leak from the e-liquid hole 113.

The sealing mechanism 13 includes a return spring 131 and a liquid stopper 132; wherein the liquid stopper 132 is connected to the atomizing sleeve 11 via the return spring 131, and before the atomizing core 12 being inserted into the atomizing sleeve 11, the liquid stopper 132 is arranged on an outer side of the e-liquid hole 113 to seal the e-liquid hole 113.

While the atomizing core 12 is inserted into the atomizing sleeve 11, the liquid stopper 132 is pushed to overcome an elastic force of the return spring 131 to open the e-liquid hole 113, and the return spring 131 is in a compressed state, as specifically illustrated in FIG. 1. When the atomizing core 12 is removed from the atomizing sleeve 11, the compressed return spring 131 restores, and the liquid stopper 132 is subjected to the elastic force of the return spring 132 to seal the e-liquid hole 113, as specifically illustrated in FIG. 2.

The atomizing sleeve 11 further includes an air pipe portion 111 and a connection portion 112; wherein a head end of the air pipe portion 111 is connected to a mouthpiece 200 and a tail end of the air pipe portion 111 is connected to a head end of the connection portion 112; and the atomizing core 12 is inserted into the connection portion 112 via the tail end of the connection portion 112, and then connected to the tail end of the air pipe portion 111.

In addition, a silica gel pad 14 is arranged between the atomizing core 12 and the tail end of the air pipe portion 111, which achieves a sealing effect in the course where aerosol generated by the atomizing core 12 enters the mouthpiece 200 via the air pipe portion 111. A tail end of the atomizing core 12 is provided with an electrode 121 to connect a battery device. The atomizing core 12 includes a heating wire 122 and a liquid absorbing cotton 123. The liquid absorbing cotton 123 is wound the heating wire 122. The heating wire 122 generates heat under the effect of the battery device, and heats and bakes the e-liquid in the liquid absorbing cotton 123 to generate the aerosol.

The e-liquid hole 113 is arranged at the tail end of the connection portion 112, and the liquid stopper 132 is correspondingly arranged on an outer side of the connection portion 112 to seal the e-liquid hole 113. The return spring 131 is arranged at the tail end of the air pipe portion 111, and the return spring 131 and the liquid stopper 132 are connected via a movable guiding sleeve 133.

The movable guiding sleeve 133 is sleeved over an outer surface of the air pipe portion 111 and an outer surface of the connection portion 112; wherein the outer surface of the air pipe portion 111 and the outer surface of the connection portion 112 are connected to form a cylindrical surface, such that when the atomizing device 100 switches from the state as illustrated in FIG. 1 to the state as illustrated in FIG. 2, the movable guiding sleeve 133 is capable of more smoothly sliding.

The atomizing device 100 further includes a steel sleeve 15; wherein the atomizing sleeve 11 is fixedly arranged in the steel sleeve 15, and the atomizing core 12 is inserted into the atomizing sleeve 11 and then thread-connected to the steel sleeve 15, thereby achieving fixing.

In this illustrated embodiment, the sealing mechanism 13 in the atomizing device 100 is configured to prevent the e-liquid from leaking from the e-liquid hole 113 when the atomizing core 12 is removed from the atomizing sleeve 11, which solves the problem of leakage of the e-liquid from the e-liquid hole 113. Therefore, detailed above mainly describes connections of the atomizing sleeve 11, the atomizing core 12 and the sealing mechanism 13, and operation manner of the sealing mechanism 13; and other elements or parts in the atomizing device 100 are not described any further.

In practice, the electronic cigarette having the atomizing device 100 further includes a battery device; wherein the battery device is electrically connected to the atomizing core in 12 the atomizing device 100, such that the atomizing core 12 heats and atomizes the e-liquid.

The atomizing device 100 according to this disclosure includes: the atomizing sleeve 11 with the e-liquid hole 113; the atomizing core 12, removably arranged in the atomizing sleeve 11; and the sealing mechanism 13, including a return spring 131 and a liquid stopper 132, the liquid stopper 132 being connected to the atomizing sleeve 11 via the return spring 131 and sealing the e-liquid hole 113; wherein when the atomizing core 12 is inserted into the atomizing sleeve 11, the liquid stopper 132 is pushed to overcome an elastic force of the return spring 131 to open the e-liquid hole 113; and when the atomizing core 12 is removed from the atomizing sleeve 11, the liquid stopper 132 seals the e-liquid hole 113 under the elastic force of the return spring 131. In the atomizing device 100 according to the disclosure, during dismantle and replacement of the atomizing core 12, the e-liquid stopper 132 seals the e-liquid hole 113, such that the e-liquid would not leak from the e-liquid hole 113, thereby facilitating user operations and improving user experience.

Described above are exemplary embodiments of this disclosure, but are not intended to limit the scope of this disclosure. Any equivalent structure or equivalent process variation made based on the specification and drawings of this disclosure, which is directly or indirectly applied in other related technical fields, fall within the scope of the disclosure.

What is claimed is:

1. An atomizing device for an electronic cigarette, comprising:
    an atomizing sleeve, defining an e-liquid hole;
    an atomizing core, removably arranged in the atomizing sleeve; and
    a sealing mechanism, comprising a return spring and a liquid stopper, the liquid stopper connected to the atomizing sleeve via the return spring and configured to seal the e-liquid hole, wherein the liquid stopper is arranged on an outer side of the e-liquid hole;
    wherein when the atomizing core is received in the atomizing sleeve, the liquid stopper overcomes an elastic force of the return spring to open the e-liquid hole; and when the atomizing core is removed from the atomizing sleeve, the liquid stopper seals the e-liquid hole under the elastic force of the return spring.

2. The atomizing device according to claim 1, wherein the atomizing sleeve further comprises: an air pipe portion and a connection portion; wherein
    a head end of the air pipe portion is connected to a mouthpiece and a tail end of the air pipe portion is connected to a head end of the connection portion; and the atomizing core is inserted into the connection portion via a tail end of the connection portion, and then connected to the tail end of the air pipe portion.

3. The atomizing device according to claim 2, wherein a tail end of the atomizing core comprises an electrode configured to connect a battery device.

4. The atomizing device according to claim 2, wherein the e-liquid hole is arranged at the tail end of the connection portion; and the liquid stopper is arranged on an outer side of the connection portion and seals the e-liquid hole when the atomizing core is removed from the atomizing sleeve.

5. The atomizing device according to claim 4, wherein the return spring is arranged at the head end of the air pipe portion, the liquid stopper is arranged at the tail end of the connection portion, and the return spring and the liquid stopper are connected via a movable guiding sleeve.

6. The atomizing device according to claim 5, wherein the movable guiding sleeve is sleeved over an outer surface of the air pipe portion and an outer surface of the connection portion, the outer surface of the air pipe portion and the outer surface of the connection portion being connected to form a cylindrical surface.

7. The atomizing device according to claim 2, wherein a silica gel pad is arranged between the tail end of the air pipe portion and the atomizing core when the atomizing core is inserted into the atomizing sleeve.

8. The atomizing device according to claim 1, wherein the atomizing device further comprises a steel sleeve, wherein the atomizing sleeve is fixedly arranged in the steel sleeve, and the atomizing core is thread-connected to the steel sleeve when the atomizing core is inserted into the atomizing sleeve.

9. The atomizing device according to claim 1, wherein the atomizing core comprises a heating wire and a liquid absorbing cotton, the liquid absorbing cotton being wound the heating wire.

10. An electronic cigarette, comprising a battery device and an atomizing device, the atomizing device comprising:
    an atomizing sleeve, comprising an air pipe portion and a connection portion, wherein a head end of the air pipe portion is connected to a mouthpiece, and a tail end of the air pipe portion is connected to a head end of the connection portion, an e-liquid hole is arranged at a tail end of the connection portion;
    an atomizing core, removably arranged in the atomizing sleeve, the battery device electrically connected to the atomizing core, wherein the atomizing core is inserted into the connection portion via the tail end of the connection portion, and then connected to the tail end of the air pipe portion: and
    a sealing mechanism, comprising a return spring and a liquid stopper, the liquid stopper arranged on an outer side of the connection portion, and connected to the atomizing sleeve via the return spring, wherein the liquid stopper is configured to seal the e-liquid hole when the atomizing core is removed from the atomizing sleeve, wherein the liquid stopper's arranged on an outer side of the e-liquid hole;
    wherein when the atomizing core is received in the atomizing sleeve, the liquid stopper overcomes an elastic force of the return spring to open the e-liquid hole; and when the atomizing core is removed from the atomizing sleeve, the liquid stopper seals the e-liquid hole under the elastic force of the return spring.

11. The electronic cigarette according to claim 10, wherein a tail end of the atomizing core comprises an electrode connected to the battery device.

12. The electronic cigarette according to claim 10, wherein the return spring is arranged at the head end of the air pipe portion, the liquid stopper is arranged at the tail end of the connection portion, and the return spring and the liquid stopper are connected via a movable guiding sleeve.

13. The electronic cigarette according to claim 12, wherein the movable guiding sleeve is sleeved over an outer surface of the air pipe portion and an outer surface of the connection portion, the outer surface of the air pipe portion and the outer surface of the connection portion being connected to form a cylindrical surface.

14. The electronic cigarette according to claim 10, wherein a silica gel pad is arranged between the tail end of the air pipe portion and the atomizing core when the atomizing core is received in the atomizing sleeve.

15. The electronic cigarette according to claim 10, wherein the atomizing device further comprises a steel sleeve, wherein the atomizing sleeve is fixedly arranged in the steel sleeve, and the atomizing core is thread-connected to the steel sleeve when the atomizing core is received in the atomizing sleeve.

16. The electronic cigarette according to claim 10, wherein the atomizing core comprises a heating wire and a liquid absorbing cotton, the liquid absorbing cotton being wound the heating wire.

* * * * *